(12) United States Patent
White et al.

(10) Patent No.: US 7,766,822 B2
(45) Date of Patent: Aug. 3, 2010

(54) HAND ASSISTED LAPAROSCOPIC SEAL ASSEMBLY WITH A RATCHETING MECHANISM

(75) Inventors: William J. White, West Chester, OH (US); Andrew T. Beckman, Cincinnati, OH (US)

(73) Assignee: Ethicon Endo Surgery, Inc., Cincinnati, OH (US)

( * ) Notice: Subject to any disclaimer, the term of this patent is extended or adjusted under 35 U.S.C. 154(b) by 553 days.

(21) Appl. No.: 11/714,268

(22) Filed: Mar. 6, 2007

(65) Prior Publication Data

US 2008/0221607 A1    Sep. 11, 2008

(51) Int. Cl.
  *A61B 1/06*    (2006.01)
(52) U.S. Cl. ...................................... 600/184
(58) Field of Classification Search ................. 606/201, 606/203, 204, 206, 208, 210; 215/216, 330
See application file for complete search history.

(56) References Cited

U.S. PATENT DOCUMENTS

| | | | |
|---|---|---|---|
| 4,915,500 | A | 4/1990 | Selkowitz |
| 5,098,195 | A | 3/1992 | Halyo et al. |
| 5,251,004 | A | 10/1993 | Doiron et al. |
| 5,640,977 | A | 6/1997 | Leahy et al. |
| 6,578,577 | B2 | 6/2003 | Bonadio et al. |
| 6,734,958 | B1 | 5/2004 | MacKinnon et al. |
| 7,081,089 | B2 | 7/2006 | Bonadio et al. |
| 7,297,106 | B2 | 11/2007 | Yamada et al. |
| 7,300,399 | B2 * | 11/2007 | Bonadio et al. ............. 600/208 |
| 7,393,322 | B2 * | 7/2008 | Wenchell ..................... 600/208 |
| 2004/0073090 | A1 * | 4/2004 | Butler et al. ................. 600/208 |
| 2004/0092795 | A1 | 5/2004 | Bonadio et al. |
| 2004/0154624 | A1 | 8/2004 | Bonadio et al. |
| 2005/0020884 | A1 | 1/2005 | Hart et al. |
| 2005/0148823 | A1 | 7/2005 | Vaugh et al. |
| 2005/0155611 | A1 | 7/2005 | Vaugh et al. |
| 2005/0192483 | A1 | 9/2005 | Bonadio et al. |
| 2005/0241647 | A1 * | 11/2005 | Nguyen et al. .............. 128/856 |
| 2006/0084842 | A1 * | 4/2006 | Hart et al. .................... 600/206 |
| 2006/0149306 | A1 * | 7/2006 | Hart et al. .................... 606/191 |
| 2008/0132765 | A1 * | 6/2008 | Beckman et al. ............ 600/204 |
| 2008/0146883 | A1 * | 6/2008 | Kistler et al. ................ 600/207 |
| 2008/0146884 | A1 * | 6/2008 | Beckman et al. ............ 600/208 |

(Continued)

FOREIGN PATENT DOCUMENTS

EP    1407715    4/2004

(Continued)

*Primary Examiner*—Todd E Manahan
*Assistant Examiner*—Christopher Schubert
(74) *Attorney, Agent, or Firm*—Welsh & Flaxman LLC

(57) ABSTRACT

A seal assembly for permitting hand assisted laparoscopic procedures includes a seal cap having a seal positioned within a housing. The housing includes a lower seal ring having a track which supports an upper seal ring for relative rotational motion, wherein the seal is supported between the upper seal ring and the lower seal ring for rotation between an open orientation and a closed orientation. The track includes an inner upstanding annular wall and an outer upstanding annular wall connected by a base member. A ratchet mechanism controls motion of the upper seal ring relative to the lower seal ring. The ratchet mechanism includes a ratchet arm oriented to engage a ratchet surface. The ratchet surface extends outwardly from a center of the seal assembly.

20 Claims, 11 Drawing Sheets

U.S. PATENT DOCUMENTS

2008/0208222 A1* 8/2008 Beckman et al. ............ 606/148

FOREIGN PATENT DOCUMENTS

| | | |
|---|---|---|
| EP | 1495728 | 1/2005 |
| WO | WO00/32117 | 6/2000 |
| WO | WO0179813 | 10/2001 |
| WO | WO2004/054456 | 7/2004 |

* cited by examiner

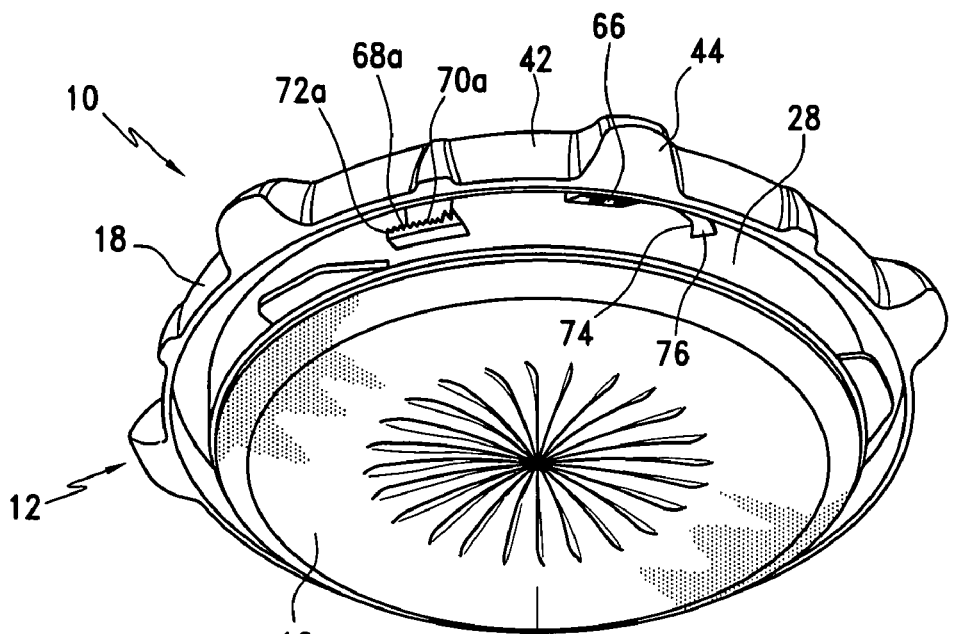
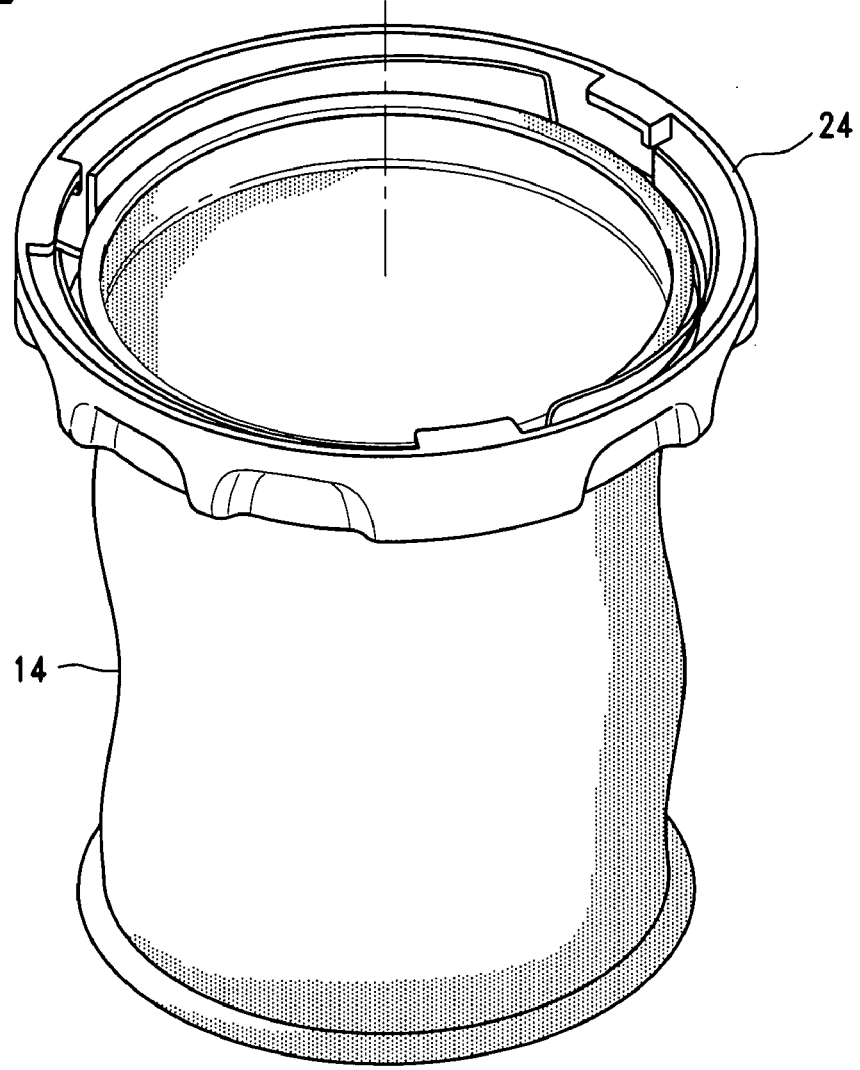
FIG. 2

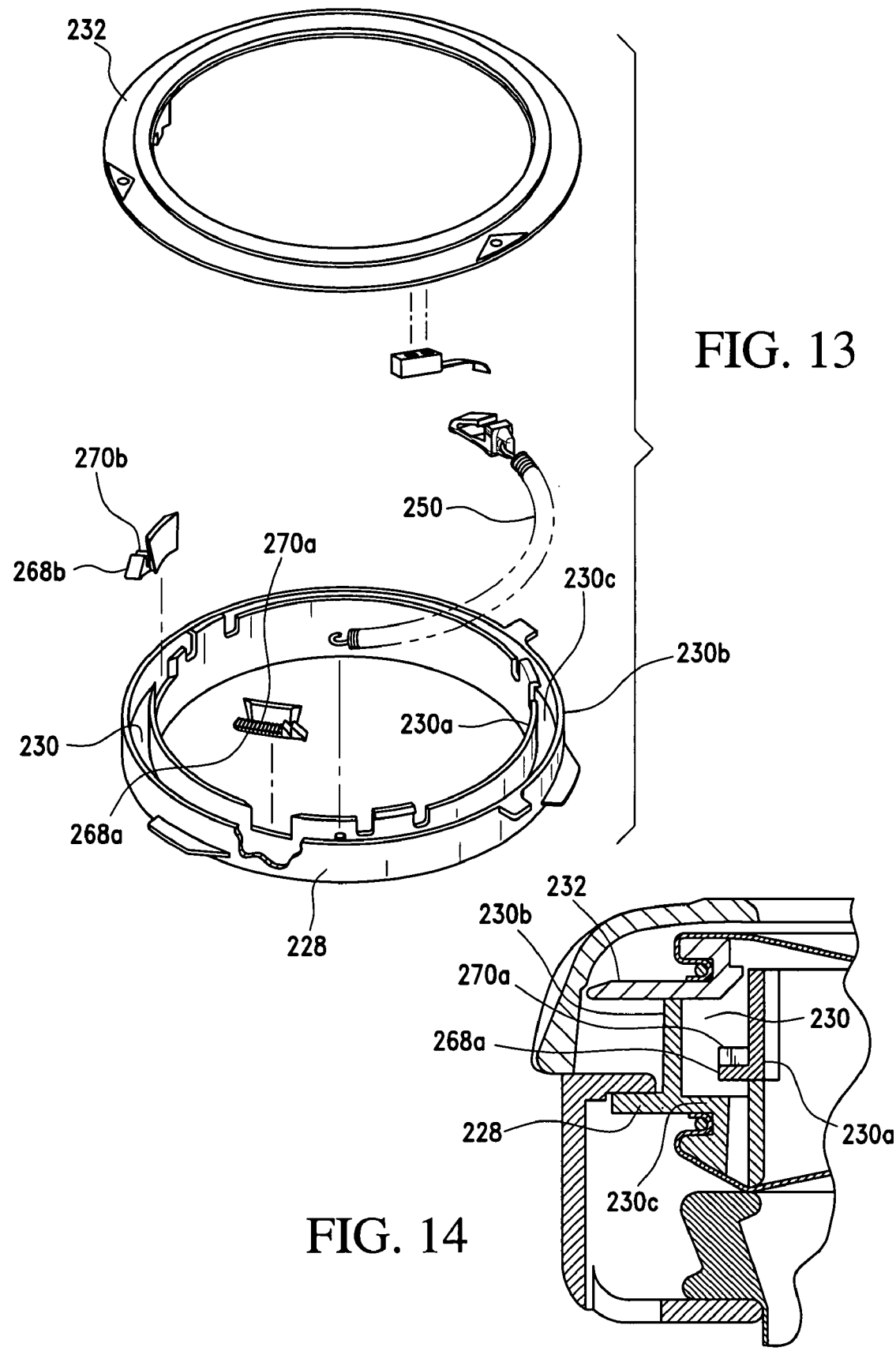

HAND ASSISTED LAPAROSCOPIC SEAL ASSEMBLY WITH A RATCHETING MECHANISM

BACKGROUND OF THE INVENTION

1. Field of the Invention

The invention relates to laparoscopic devices. In particular, the invention relates to a laparoscopic seal assembly permitting the use of hands in assisting during laparoscopic procedures.

2. Description of the Related Art

During laparoscopic procedures, it is often desirable for the surgeon to place his or her hand within the patient in a manner manipulating the instruments positioned within the patient. When this occurs, it is desirable to separate the external environment from the internal portion of the patient. For example, when hand assisted laparoscopic procedures are performed within the abdominal cavity, it is desirable to perform hand exchanges with minimal loss of abdominal pressure.

As such, a need exists for skin mountable seals permitting hand assisted laparoscopic procedures without fear that the abdominal pressure will be compromised. The present invention provides such an apparatus.

SUMMARY OF THE INVENTION

It is, therefore, an object of the present invention to provide a seal assembly for permitting hand assisted laparoscopic procedures. The seal assembly includes a seal cap having a seal positioned within a housing. The housing includes a lower seal ring having a track which supports an upper seal ring for relative rotational motion, wherein the seal is supported between the upper seal ring and the lower seal ring for rotation between an open orientation and a closed orientation. The track includes an inner upstanding annular wall and an outer upstanding annular wall connected by a base member. A ratchet mechanism controls motion of the upper seal ring relative to the lower seal ring. The ratchet mechanism includes a ratchet arm oriented to engage a ratchet surface. The ratchet surface extends outwardly from a center of the seal assembly.

It is also an object of the present invention to provide a seal assembly wherein the ratchet arm is coupled to the upper seal ring and the ratchet surface is coupled to the lower seal ring, the ratchet surface being secured along an exterior surface of the outer upstanding annular wall such that the ratchet surface extends outwardly from a center of the seal assembly.

It is another object of the present invention to provide a seal assembly wherein the ratchet arm is shaped and dimensioned to engage the ratchet surface when the upper seal ring is rotated relative to the lower seal ring in a first direction and rides under the ratchet surface when the upper seal ring is rotated relative to the lower seal ring in a second direction.

It is a further object of the present invention to provide a seal assembly wherein the ratchet arm includes a tapered distal end shaped and dimensioned to ride under the ratchet surface as the upper seal ring is rotated relative to the lower seal ring in the second direction.

It is also another object of the present invention to provide a seal assembly including first and second ratchet surfaces on the lower seal ring.

It is also a further object of the present invention to provide a seal assembly including first and second ratchet surfaces.

It is still a further object of the present invention to provide a seal assembly including a spring biasing the upper seal ring relative to the lower seal ring.

It is yet a further object of the present invention to provide a seal assembly including a retractor extending from the seal cap.

It is also another object of the present invention to provide a seal assembly wherein the housing further includes an attachment ring detachably secured to the lower seal ring for permitting selective attachment of the retractor by positioning it between the attachment ring and the lower seal ring.

It is also a further object of the present invention to provide a seal assembly wherein the lower seal ring includes at least one outwardly extending flange shaped and dimensioned for seating within at least one inwardly facing recess formed along the attachment ring.

It is also an object of the present invention to provide a seal assembly wherein an upper end of the seal is connected to the upper seal ring and a lower end of the seal is connected to the lower seal ring.

It is still another object of the present invention to provide a seal assembly including an ergonomic cover member secured to the upper seal ring, wherein the ergonomic cover member includes a contoured outer surface providing for improved handling and twisting of the upper seal ring for opening and closing the seal.

It is yet another object of the present invention to provide a seal assembly wherein the seal is an iris seal.

It is also an object of the present invention to provide a seal assembly wherein the iris seal is constructed in a folded configuration spanning the upper seal ring and the lower seal ring.

It is a further object of the present invention to provide a seal assembly wherein the iris seal is composed of a rubber like member.

It is also another object of the present invention to provide a seal assembly including a contoured ring secured to the upper seal ring, the contoured ring including an inner circumference formed with a series of recesses shaped and dimensioned for receiving fingers of a user.

It is also a further object of the present invention to provide a seal assembly wherein the outer upstanding annular wall includes a plurality of recesses shaped and dimensioned for selectively receiving the ratchet surfaces at desired locations along the lower seal ring.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a perspective view of the hand assisted laparoscopic seal assembly with the attachment ring and retractor disengaged from the seal cap.

FIGS. 13 and 14 are respectively an exploded perspective view and a cross sectional view of an alternate ratchet mechanism.

DESCRIPTION OF THE PREFERRED EMBODIMENTS

Figure 1:
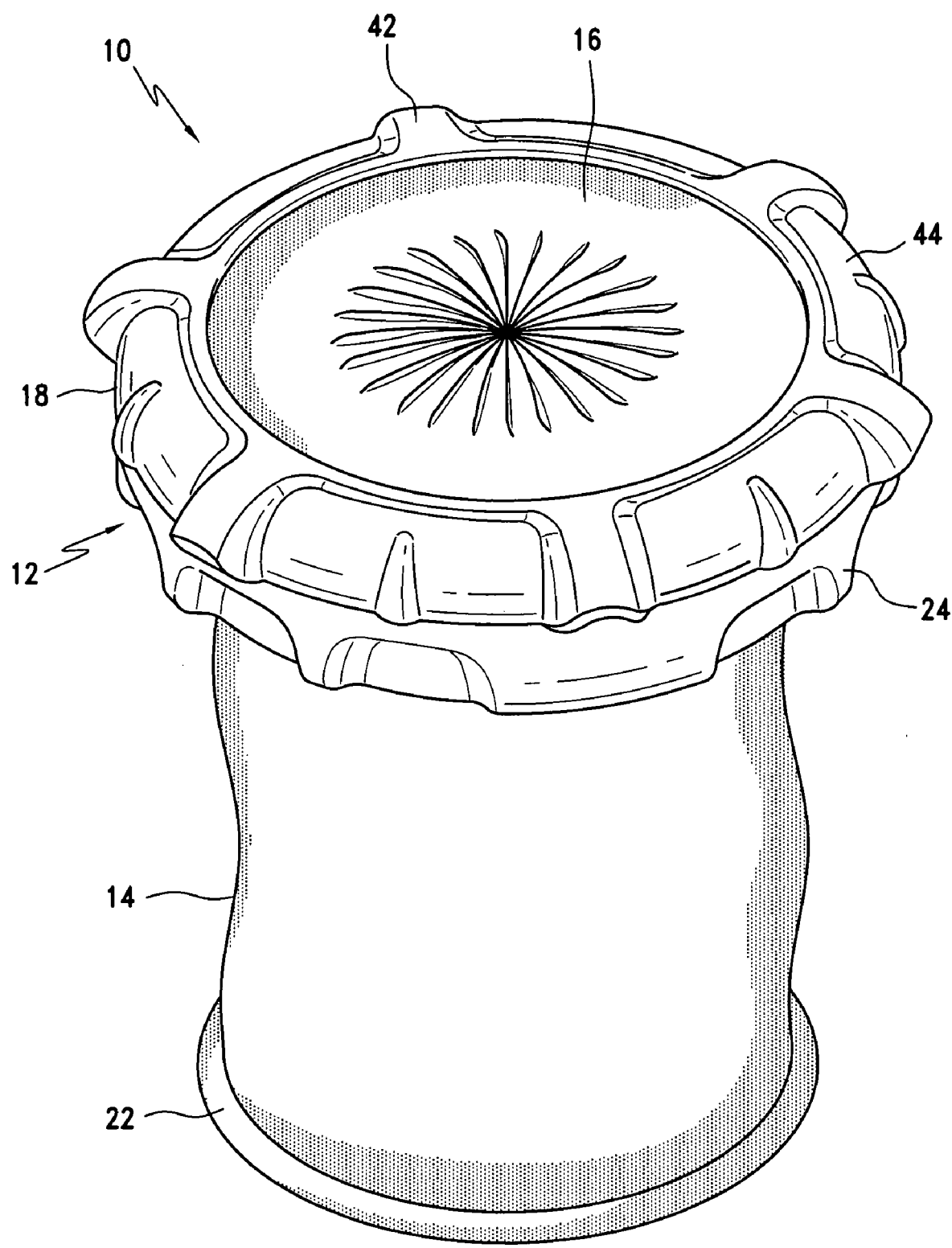
FIG. 1 is a perspective view of the present hand assisted laparoscopic seal assembly.
Figure 3:
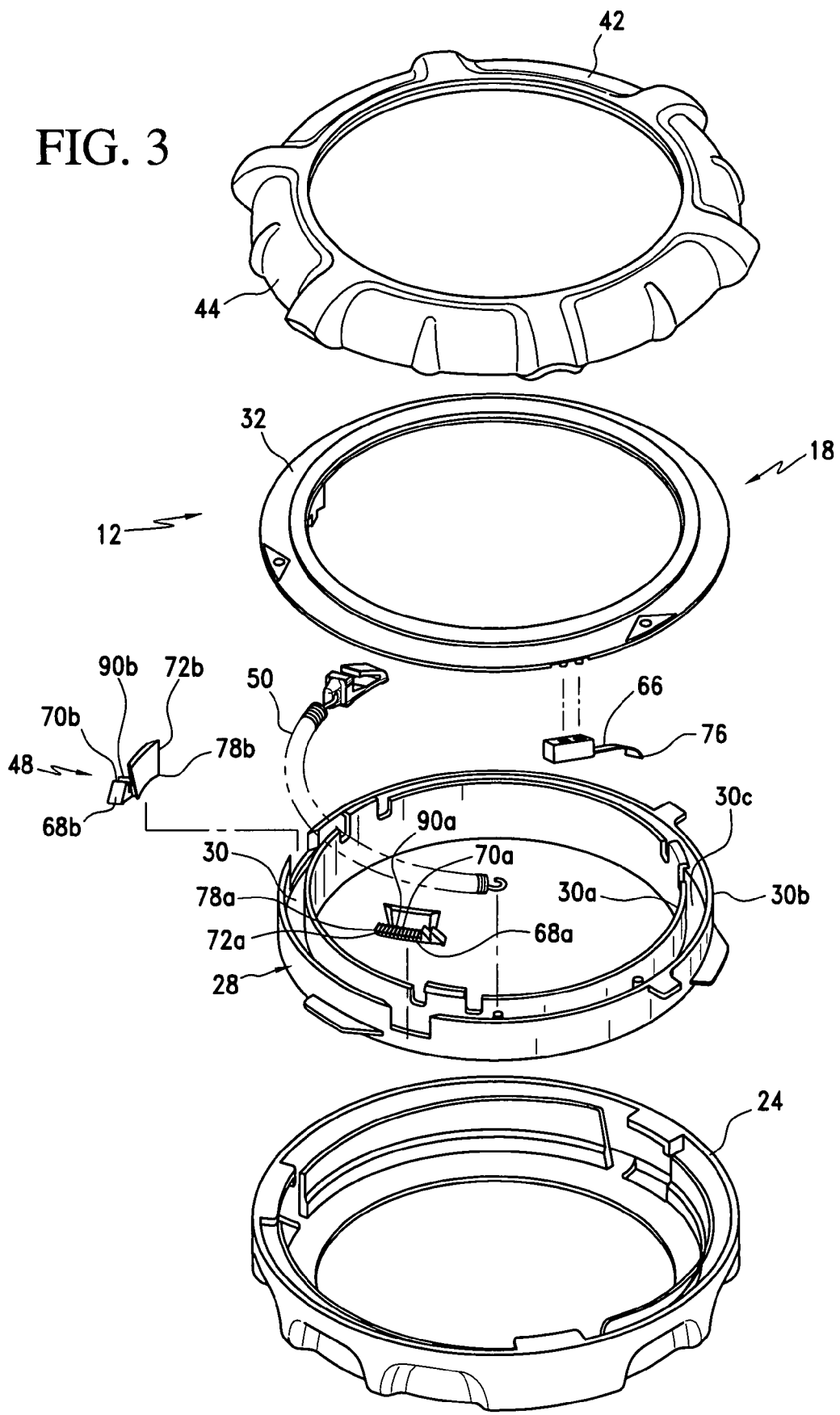
FIG. 3 is an exploded view of the seal cap of the present seal assembly.
Figure 4:
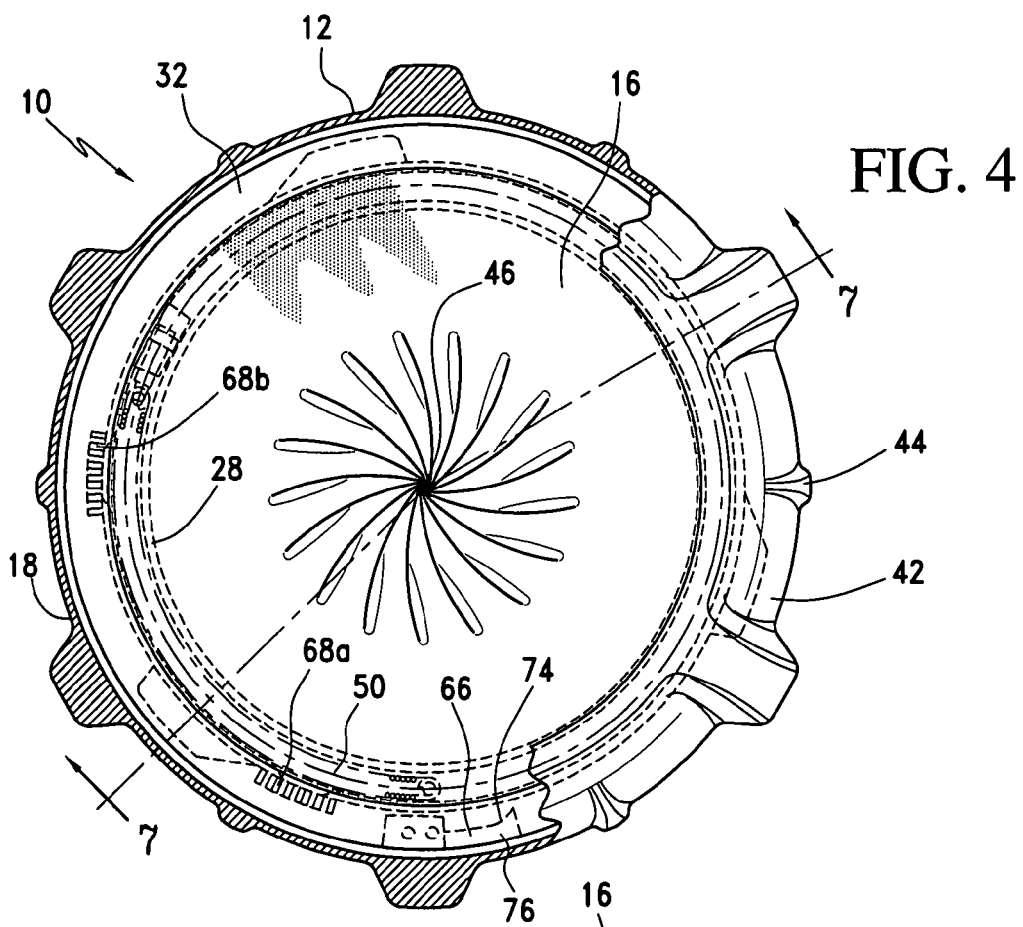
FIGS. 4, 5 and 6 are partial sectional top views showing actuation of the present hand assisted laparoscopic seal assembly respectively between a closed position, a partially opened orientation for hand insertion and a fully opened orientation for viewing and insertion of larger instruments.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 11, a seal assembly 10 for permitting hand assisted laparoscopic procedures is disclosed. The seal assembly 10 generally employs an iris seal cap 12 and retractor 14 to ensure abdominal pressure is not compromised during hand exchanges while hand assisted laparoscopic procedures are performed. As such, and in accordance with a preferred embodiment of the present invention, the seal assembly 10 includes an iris seal 16 housed within a seal cap 12. The iris seal 16 includes a central access opening 46 allowing access to the body cavity as described by the surgeon, or other medical practitioner, performing the procedure. As a result, the iris seal 16 is shaped and dimensioned to create a gas tight barrier around the surgeon's wrist when inserted through the seal assembly 10 and also creates a gas tight barrier between the interior abdominal space and the external environment when a hand is not inserted through the seal assembly 10. As will be discussed below in greater detail, adjustment of the iris seal 16, and ultimately the central access opening 46, provides for access to the body cavity in this highly controlled manner.

Referring to the various figures, the seal cap 12 includes an iris seal 16 positioned within a housing 18. The housing 18 is made of soft textured material such as the thermoplastic elastomer SANTOPRENE, or other like materials, and supports the iris seal 16 in a concentric manner. Although SANTOPRENE is disclosed in accordance with a preferred embodiment, other housing materials may be used without departing from the spirit of the present invention.

As with prior hand assisted laparoscopic seal assemblies, the housing 18 of the present seal assembly 10 is secured to the abdominal wall 20 of an individual patient by first creating an incision and positioning the retractor 14 and the seal cap 12 above the incision. Thereafter, the retractor 14, which will eventually be coupled to the seal cap 12, is inserted into the body cavity with the abdominal wall 20 therebetween. The seal cap 12 is then connected to the retractor 14 in a manner securely connecting and supporting the seal cap 12 on the outside of the abdominal wall 20 with the abdominal wall 20 resiliently held between the retractor 14 and the seal cap 12.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 14 and the present seal assembly 10. If the incision is too small, the incision is extended as required on each end to maintain the central position of the incision relative to the placement of the retractor 14 and the present seal assembly 10. Thereafter, the lower retractor ring 22 of the retractor 14 is inserted through the incision. Using one's fingers, the retractor 14 is seated evenly under the peritoneum and the area is swept to ensure the retractor 14 is not lying between tissue layers. Thereafter, the seal cap 12 is attached to the retractor 14 via an attachment ring 24, which may be rigid but not limited thereto, and adjustments are made to ensure the seal assembly 10 is secured with the patient's abdomen, maintaining pneumo. As those skilled in the art will certainly appreciate, the retractor may be a fixed length or adjustable length retractor. In either case the retractor 14 must fit the abdominal wall thickness to maintain stability and pneumo. As briefly discussed above, the present seal assembly 10 is provided with an attachment ring 24 that is detachable from the remaining portions of the housing 18 for permitting selective attachment of the retractor 14 to the present seal cap 12.

In accordance with a preferred embodiment of the present invention, the attachment ring 24 is substantially the same as those disclosed in commonly owned U.S. patent application Ser. No. 11/607,118, entitled "Hand Assisted Laparoscopic Device" which is incorporated herein by reference. However, and as those skilled in the art will certainly appreciate, other retractor attachment techniques may be employed without departing from the spirit of the present invention.

In accordance with a preferred embodiment, the iris seal 16 is a rotatable seal which selectively opens to permit passage of a surgeon's hand therethrough and automatically closes in a manner creating a gas tight barrier between the interior abdominal space and the external environment whether or not a hand or instrument 26 is inserted through the seal assembly 10. In particular, the housing 18 in which the iris seal 16 is supported includes a lower seal ring 28 having a track 30 which supports an upper seal ring 32 for relative rotational motion in a manner discussed below in greater detail.

As will be discussed below in greater detail, the upper end 34 of the iris seal 16 is permanently connected to the upper seal ring 32. The lower end 36 of the iris seal 16 is permanently connected to the lower seal ring 28. The upper seal ring 32 and the lower seal ring 28 are connected together for relative rotational movement in a manner allowing for opening and closing of the iris seal 16. In accordance with a preferred embodiment, the upper seal ring 32 and the lower seal ring 28 are connected by at least three snap tabs 38 located on the lower seal ring 28 that are shaped and dimensioned to engage a recess 40 along the inner edge of the upper seal ring 32.

An ergonomic cover member 42 is secured to the upper seal ring 32. The ergonomic cover member 42 includes a contoured outer surface 44 providing for improved handling and twisting of the upper seal ring 32 for opening and closing the iris seal 16 in accordance with the present invention. In accordance with a preferred embodiment, the ergonomic cover member 42 is a separate component fixedly secured to the upper seal ring 32 such that rotational force applied to the ergonomic cover member 42 is transmitted onto the upper seal ring 32 for opening and closing of the iris seal 16. However, and as those skilled in the art will certainly appreciate, the ergonomic cover member 42 could be integrally formed with the upper seal ring 32, while still remaining within the spirit of the present invention.

Referring to FIGS. 4, 5, 6, 7 and 8, as discussed below in greater detail, the iris seal 16 is secured between the upper seal ring 32 and the lower seal ring 28. The upper seal ring 32 is supported within a track 30 of the lower seal ring 28 in a manner facilitating rotational movement between the upper seal ring 32 and the lower seal ring 28. In this way, the rotational movement of the upper seal ring 32 relative to the lower seal ring 28 is utilized to control the opening and closing of the iris seal 16 for one-hand insertion of a hand through the present seal assembly 10.

The iris seal 16 is mounted between the upper seal ring 32 and the lower seal ring 28 such that upon rotation of the upper seal ring 32 in a predetermined direction, the central access opening 46 of the iris seal 16 will open providing a surgeon with a central access opening 46 for passage of his hand therethrough. Automatically the upper seal ring 32, and ultimately, the iris seal 16 will rotate in the reverse direction, the central access opening 46 will close securely about the wrist of the surgeon or instrument. That is, the upper seal ring 32 and the iris seal 16 are moved between open orientations (see FIGS. 5, 6 and 8) in which a central access opening 46 is created within the iris seal 16 and a closed orientation (see FIGS. 4 and 7) in which the iris seal 16 is either wrapped about the wrist of a user with his or her hand inserted therein or substantially fully closed when the iris seal 16 is not in use.

Opening and closing of the iris seal 16 is achieved by constructing the iris seal 16 in a folded configuration spanning the upper seal ring 32 and the lower seal ring 28 in a substantially taut configuration. As such, rotation of the upper seal ring 32 in a first direction will result in an increase of tension along the iris seal 16 in a manner drawing the fold outwardly opening the central access opening 46 in the iris seal 16.

Figure 7:
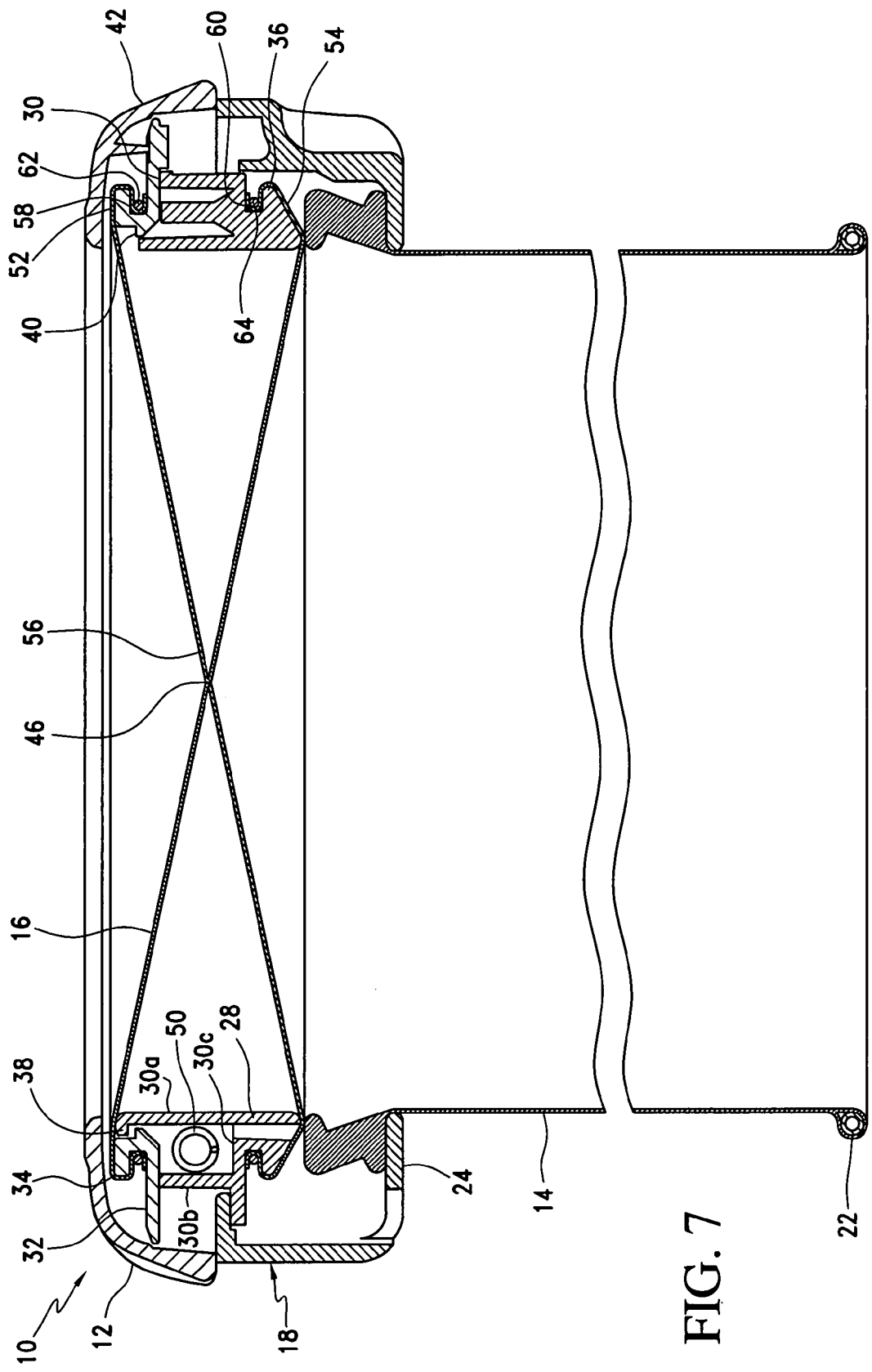
FIG. 7 is cross sectional view taken along the line 7-7 in FIG. 4.
Figure 8:
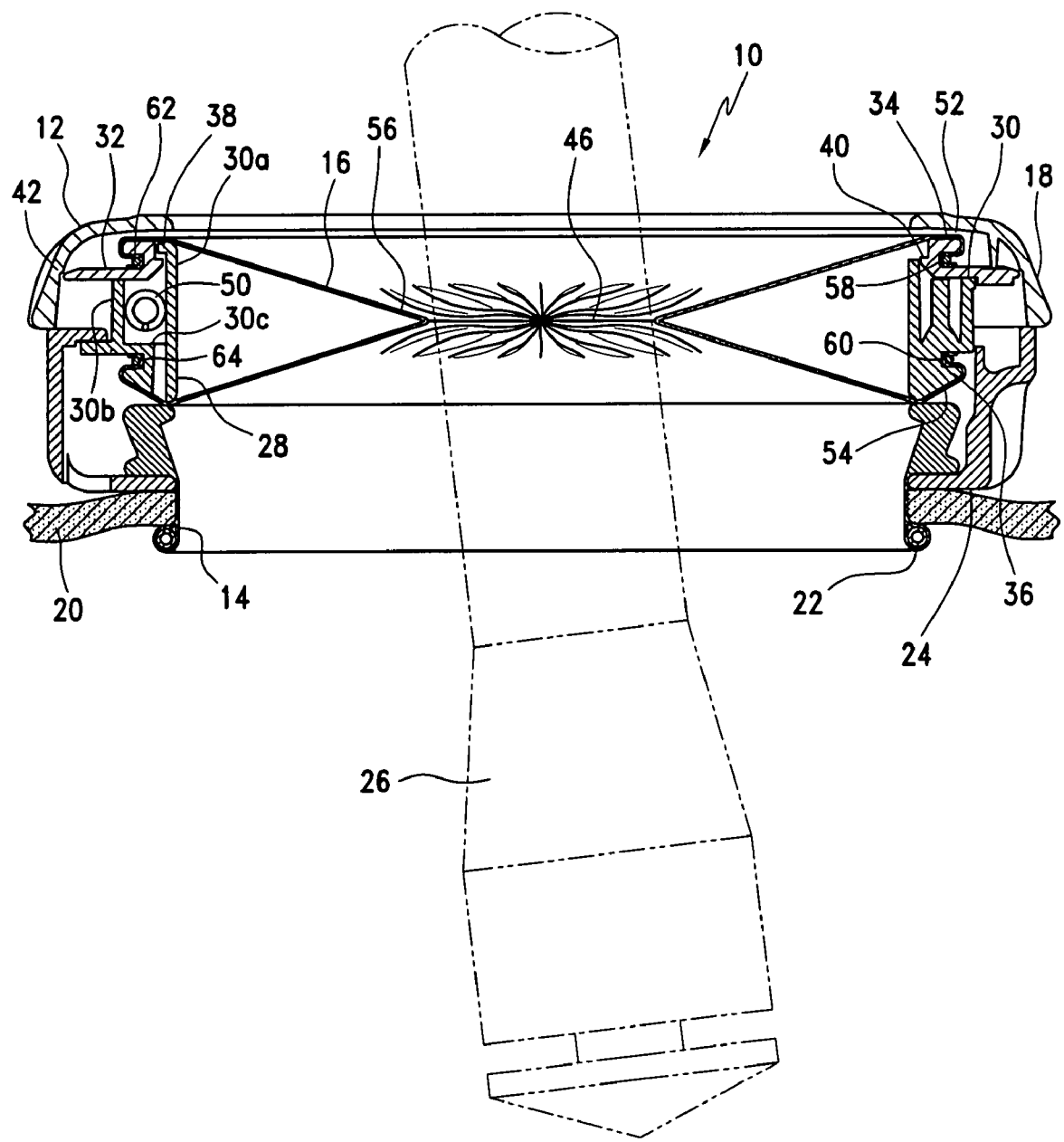
FIG. 8 is cross sectional view taken along the line 8-8 in FIG. 6 with an instrument shown in phantom.

In accordance with the preferred embodiment, the iris seal 16 is composed of a rubber like member. The rubber like member is constructed in the shape of a cylindrical section with the upper and lower sections 52, 54 thereof having a wider diameter than the central section 62 (thereby offering a cross section as shown in FIGS. 7 and 8 when assembled). As will be appreciated based upon the following disclosure, the construction of the rubber like member creates a substantially planar iris seal 16 which is closed or opened when the upper seal ring 32 and the lower seal ring 28 are rotated relative to one another in opposite directions.

In accordance with a preferred embodiment, the rubber like member is formed from a thin film having a thickness less than 0.025" and made from a material having elasticity, such as, natural rubber, synthetic rubber, poly vinyl chloride, silicon and a variety of elastomers (for example, urethane, polyisoprene, silicone). As briefly mentioned above, the rubber like member is tapered cylindrically and includes a central access opening 46 having a predetermined cross sectional area at the central section 56 thereof. The rubber like member is shaped such that the diameter of the opening decreases in the direction from the upper and lower sections to the central section 56 of the rubber like member. Furthermore, the upper and lower ends 52, 54 of the iris seal 16, which are fitted into the grooves 58, 60 of the upper seal ring 32 and the lower seal ring 28 and held therein with O-rings 62, 64, allow for detachment from the upper seal ring 32 and the lower seal ring 28. In accordance with a preferred embodiment, the O-rings are integrated into the iris seal, minimizing components and material cost. Because of such detachable structure of the rubber like member, it can be easily replaced by a fresh member when the used rubber like member is broken or worn. This technique would be useful for reusable devices.

Figure 5:
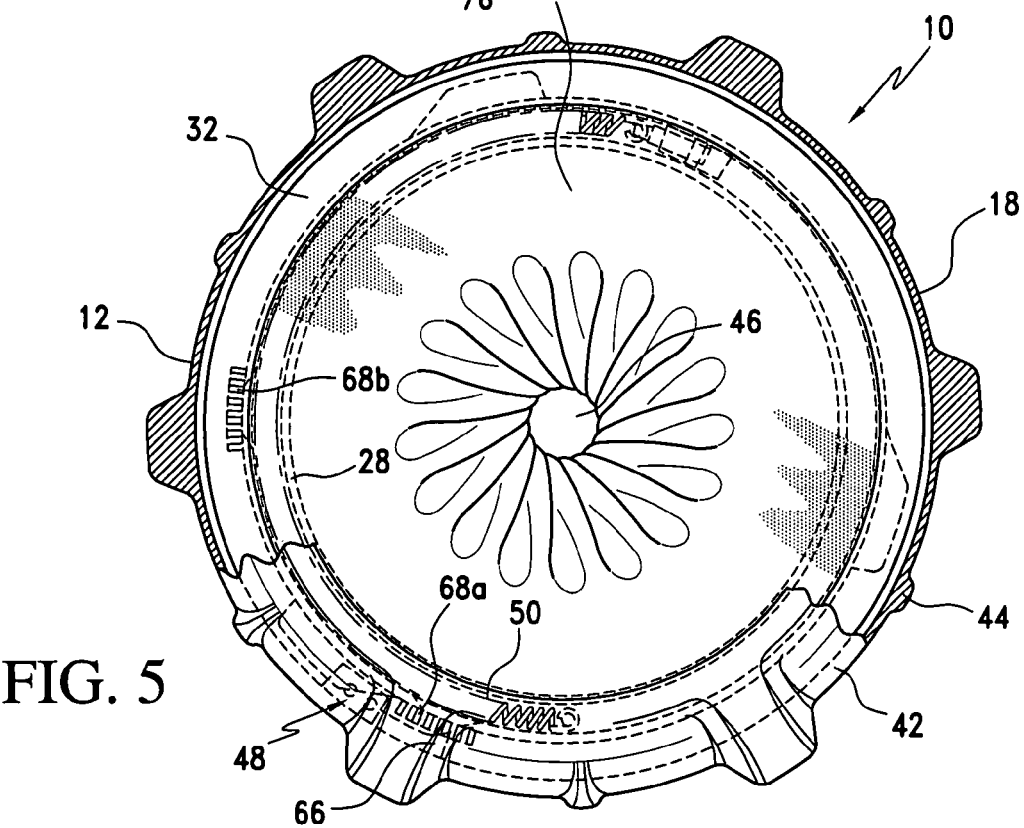
Figure 6:
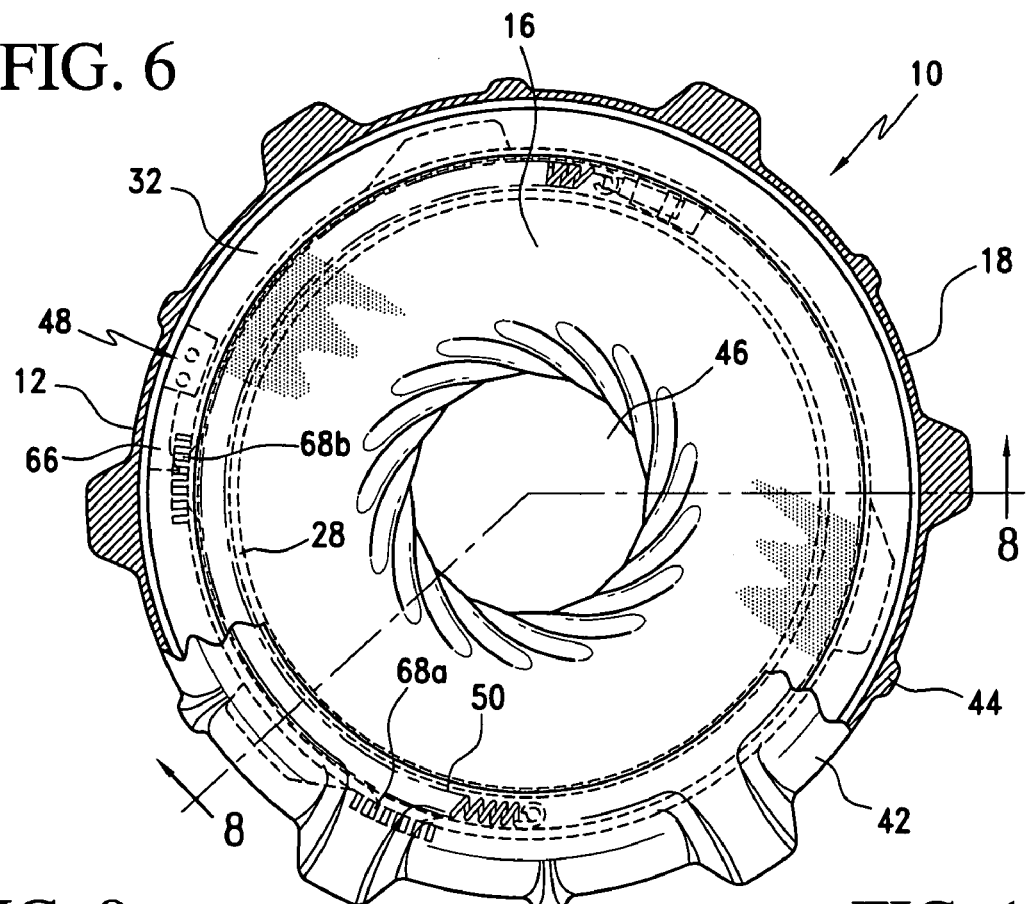
Figures 9, 10:
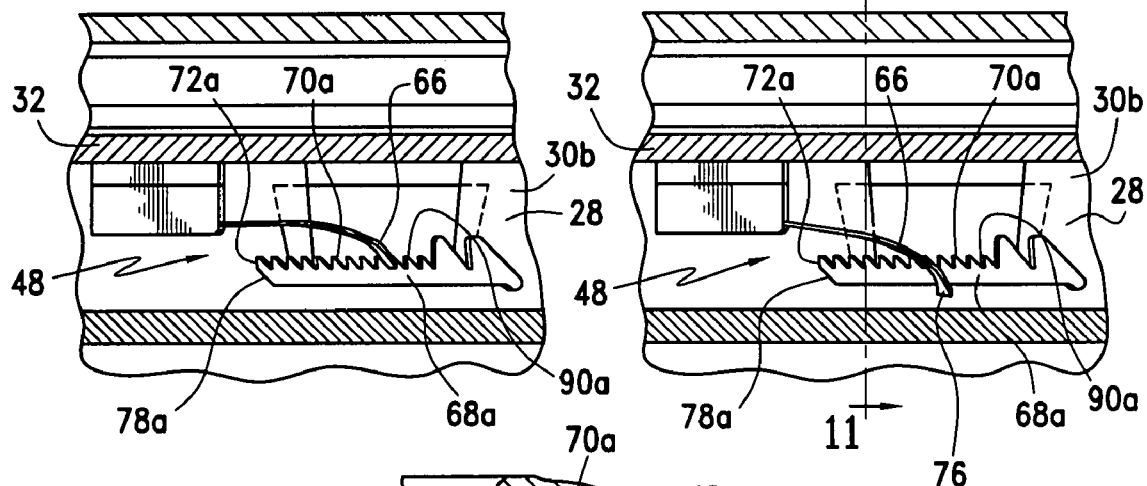
FIGS. 9, 10 and 11 are detailed views of the ratchet mechanism in accordance with the present invention.
Figure 11:
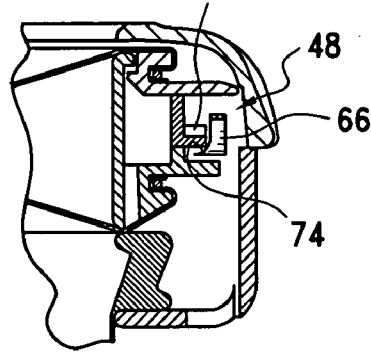

Referring to FIGS. 4, 5, 6, 7 and 8, a plan view and a sectional view are presented, showing the iris seal 16 in its respective closed and open states. FIGS. 6 and 8 show the iris seal 16 in a fully opened orientation for viewing within the cavity or insertion of an instrument or hand therethrough, while FIG. 5 shows a partially opened orientation sufficient for passing a hand therethrough when sealing thereabout is desired.

This open state is created when the upper seal ring 32 is rotated at a predetermined angle, for example, 15 degrees, from the closed state of the iris seal 16, and the central access opening 46 is created.

Figure 12:
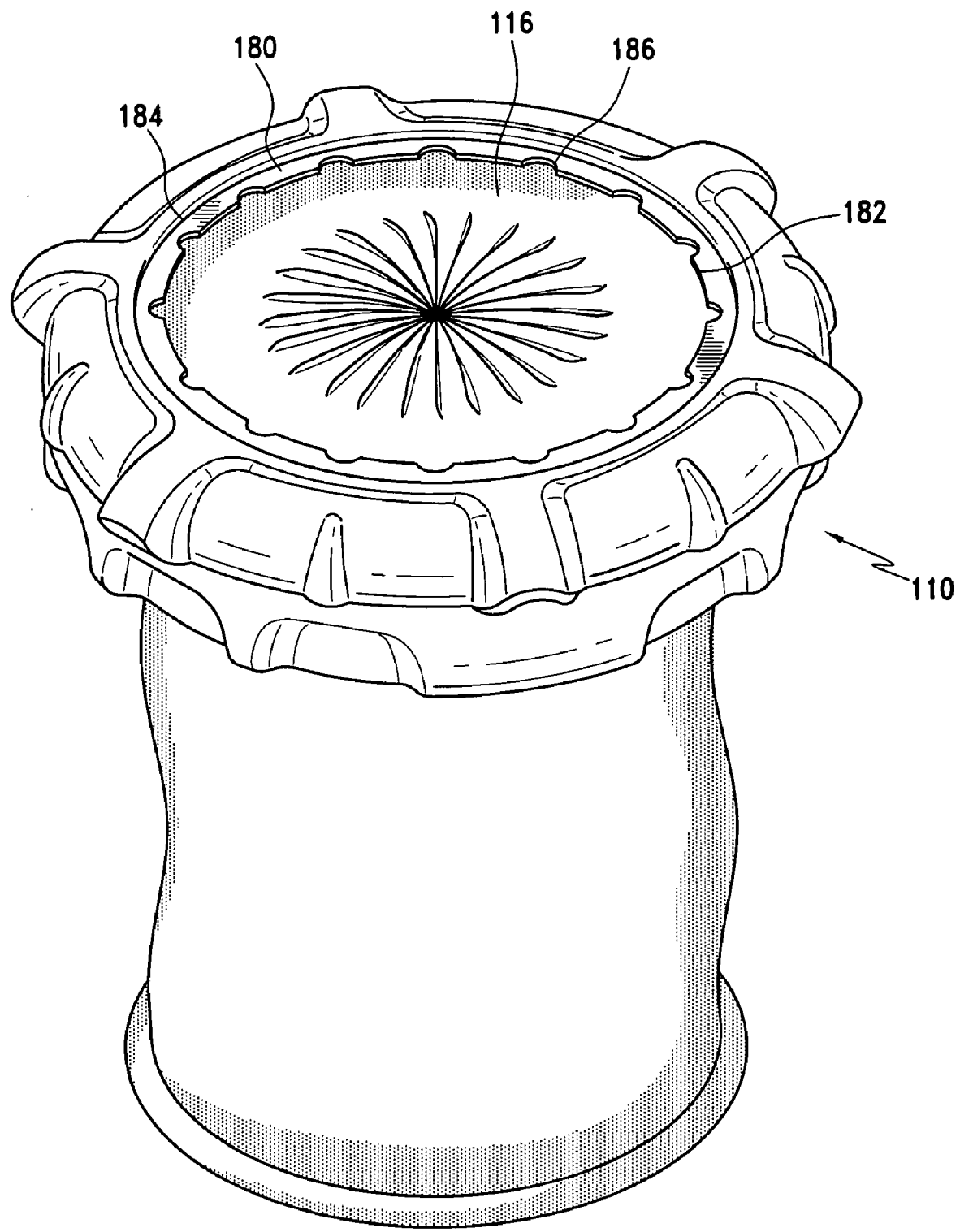
FIG. 12 is a perspective view of a seal assembly in accordance with an alternate embodiment.
Figure 15:
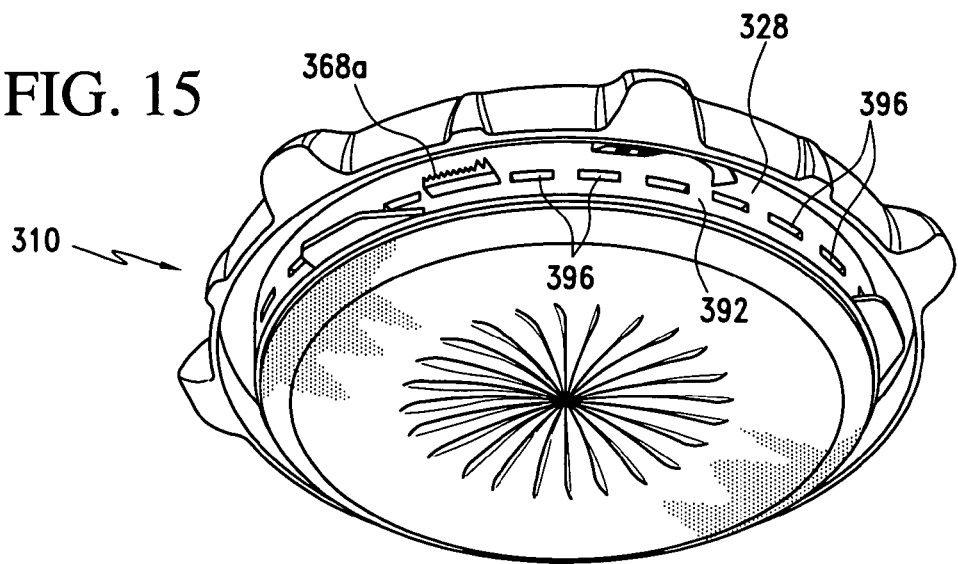
FIGS. 15, 16, 17 and 18 are respectively a perspective view, an exploded perspective view, a top view and a cross sectional view of yet another ratchet mechanism in accordance with another ratchet mechanism.
Figure 16:
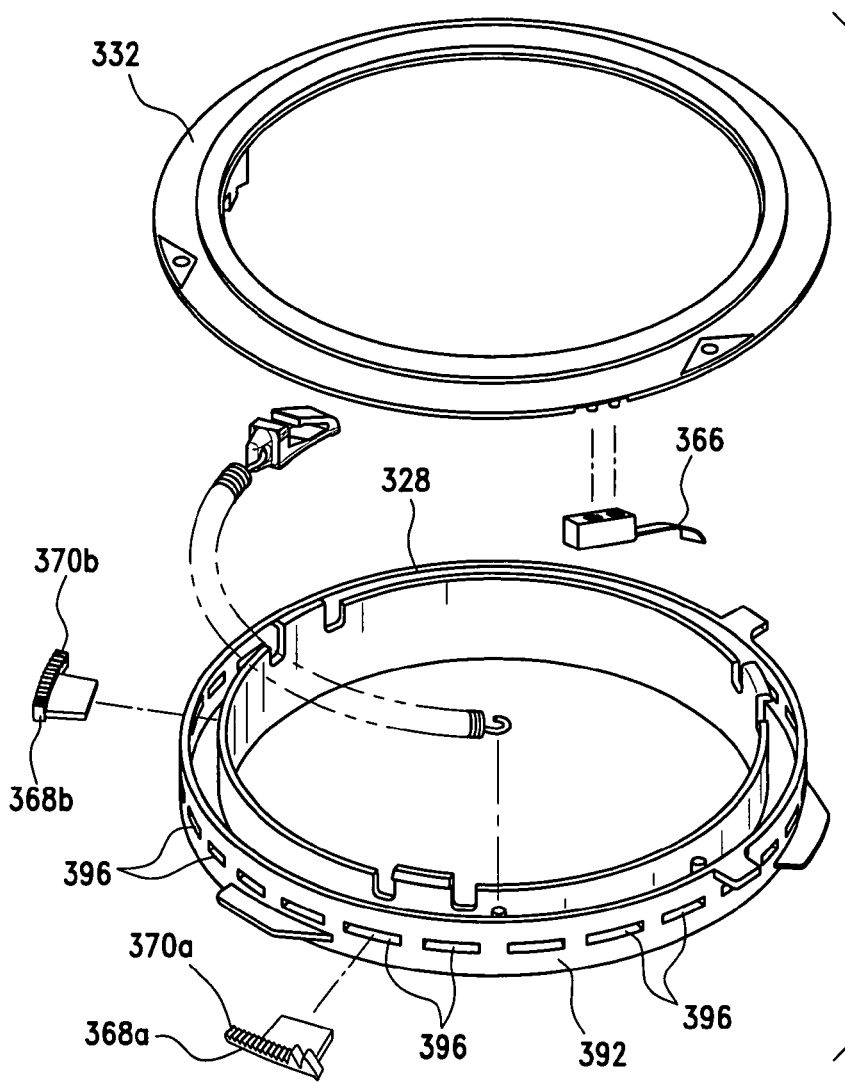
Figure 17:
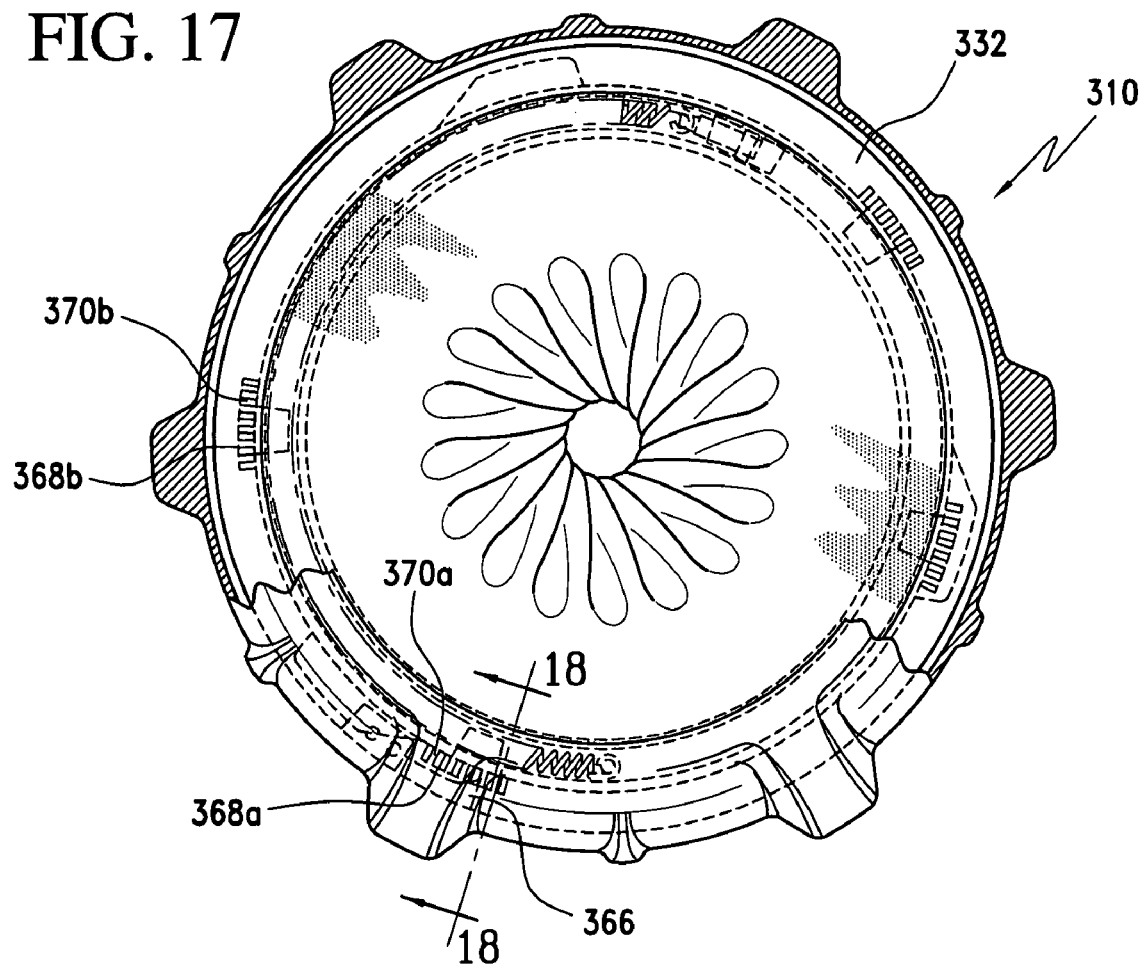
Figure 18:
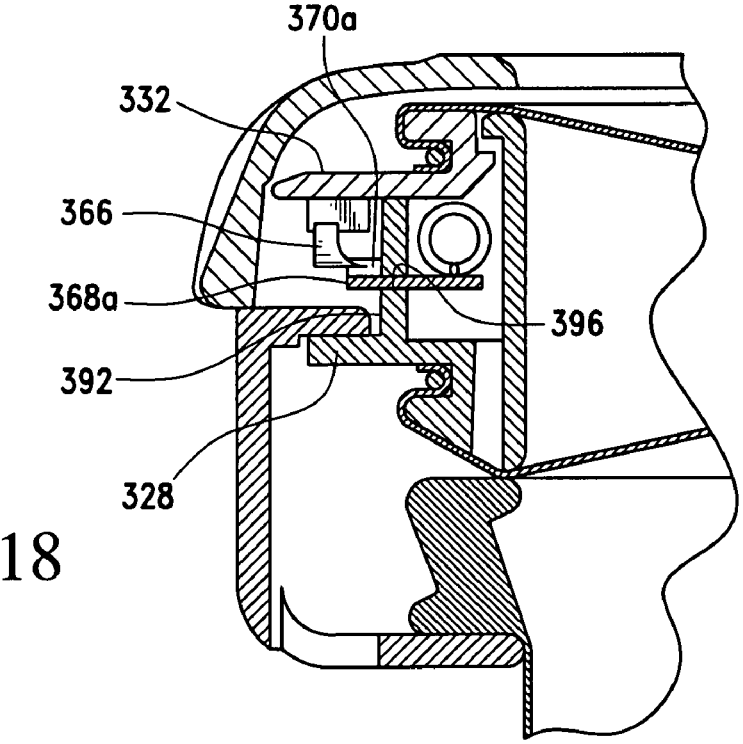

In accordance with an alternate embodiment, and with reference to FIG. 12, improved manual movement of the upper seal ring 132, and ultimately, the iris seal 116, is achieved by the provision of a contoured ring 180 secured to the upper surface of the upper seal ring 132. The contoured ring 180 is substantially annular and includes an inner circumference 182 and an outer circumference 184. The outer circumference 184 is substantially smooth and conforms to the profile of the upper seal ring. However, the inner circumference 182 is formed with a series of recesses 186 shaped and dimensioned for receiving the fingers of a medical practitioner attempting to use the present seal assembly 110. In particular, the series of recesses 186 are shaped and dimensioned such that an individual wishing to use the present seal assembly 110 may seat his or her fingers therein and rotate the contoured ring 180, and the upper seal ring 132 to which the contoured ring 180 is rigidly attached, and ultimately the iris seal 116 with only one hand. While the iris seal 116 is in its open orientation, the user may simply slip his or her hand through the iris seal 116 and proceed with the surgical procedure with minimal loss of insufflation. This feature allows the physician's other hand to be free and undisrupted, allowing the surgeon to maintain his procedural focus and position with the free hand during hand exchanges.

In accordance with a preferred embodiment, the upper seal ring 32 is biased relative to the lower seal ring 28 by a spring 50 to immediately return to the closed orientation upon rotation of the upper seal ring 32 relative to the lower seal ring 28 to its open orientation with subsequent release thereof. As such, the surgeon may rotate the upper seal ring 32 relative to the lower seal ring 28 through engagement of the contoured surface of the ergonomic cover member 42, the contoured ring 180 (in accordance with the embodiment shown with reference to FIG. 12) or by engaging the iris seal 16 directly to move the iris seal 16 from its closed orientation to an open orientation opening the central access opening 46 for passage of his or her hand therethrough. Once his or her hand is passed therethrough, the upper seal ring 32, ergonomic cover member 42, contoured ring 180 and/or the iris seal 16 are released allowing the action of the spring 50 to move the upper seal ring 32 and the iris seal 16 back toward the closed orientation.

As some surgeons may want to maintain an open orientation using the auto-closing device, a ratchet mechanism 48 has been developed wherein the surgeon needs control over the spring biased action moving the upper seal ring 32 relative to the lower seal ring 28 and iris seal 16 from its open orientation to its closed orientation.

In accordance with a preferred embodiment, and with reference to FIGS. 3 to 11, the upper seal ring 32 is seated within the track 30 of the lower seal ring 28 with the spring 50 biasing the upper seal ring 32 relative to the lower seal ring 28 for movement relative thereto opening the central access opening 46. However, a ratchet mechanism 48 is positioned between the upper seal ring 32 and the lower seal ring 28. The ratchet mechanism 48 includes a ratchet arm 66 secured to the upper seal ring 32 which is oriented to engage upwardly facing first and second ratchet surfaces 68a, 68b composed of a plurality of ratchet teeth 70a, 70b on the lower seal ring 28 which functions to hold the upper seal ring 32 relative to the lower seal ring 28 as it is moved to an open orientation. In practice, the ratchet arm 66 is shaped and dimensioned to engage the ratchet teeth 70a, 70b of the first and second ratchet surfaces 68a, 68b when the upper seal ring 32 is rotated in a first direction (for example, and in accordance with a preferred embodiment, clockwise rotation when viewed from above). However, once the upper seal ring 32 is rotated such that the ratchet arm 66 moves beyond the rear end 72a, 72b of the first and second ratchet surfaces 68a, 68b, the ratchet arm 66 is free to move under the first and second ratchet surfaces 68a, 68b as the upper seal ring 32 is rotated in a second direction opposite the first direction.

This is achieved by providing the ratchet arm 66 with a tapered distal end 76 which is biased by a similar tapered surface 78a, 78b on the respective rear end 72a, 72b of the first and second ratchet surfaces 68a, 68b to ride under the first and second ratchet surfaces 68a, 68b as the upper seal ring 32 is rotated relative to the lower seal ring 28 in a second direction. However, when the upper seal ring 32 is rotated in a first direction, the distal end 76 of the ratchet arm 66 is biased to ride over the upper surface of the first and second ratchet surfaces 68a, 68b such that it engages the various ratchet teeth 70a, 70b to control movement of the upper seal ring 32 relative to the lower seal ring 28.

In accordance with a preferred embodiment, the track 30 includes an inner upstanding annular wall 30a and an outer upstanding annular wall 30b connected by an annular base member 30c. As discussed above, the ratchet mechanism 48 includes a ratchet arm 66 coupled to the upper seal ring 32. The ratchet arm 66 is oriented to engage the first and second ratchet surfaces 68a, 68b coupled to lower seal ring 28. The first and second ratchet surfaces 68a, 68b are secured to extend from an exterior surface of the outer upstanding annular wall 30b such that the first and second ratchet surfaces 68a, 68b extend outwardly from a center of the seal assembly 10.

In accordance with a preferred embodiment of the present invention, first and second ratchet surfaces 68a, 68b are provided. The first ratchet surface 68a engages the ratchet arm 66 when the upper and lower seal rings 32, 28 are oriented to provide a relatively small opening in the iris seal 16 through which a medical practitioner may pass his or her hand to gain access to a body cavity. The configuration is especially suited to single hand interactions where a user may rotate the upper seal ring 32 relative to the lower seal ring 28 with the same hand which is to be passed through the present seal assembly 10. In particular, and as a result of the ratchet mechanism 48, a user may, for example, use his or her left hand to rotate the upper seal ring 32 relative to the lower seal ring 28 in a manner slightly or partially opening the iris seal 16 as shown in FIG. 5. When in this position, the audible click sound and slight resistance produced as the ratchet arm 66 moves over the first ratchet surface 68a will provide the user with an indication a stopping position has been reached. At this point, the user may release the upper seal ring 32 without fear that the iris seal 16 will snap back to its closed orientation. Rather, the ratchet mechanism 48 holds the upper and lower seal rings 32, 28 relative to each other, allowing the user to slip his or her hand through the central access opening 46 created in the iris seal 16. As the user pushes his or her hand through the iris seal 16, the outward force causes a slight rotation of the upper seal ring 32 relative to the lower seal ring 28 in a manner disengaging the ratchet arm 66 from the first ratchet surface 68a, and allowing the upper seal ring 32 to rotate relative to the lower seal ring 28 under the bias of the spring 50 to move the iris seal 16 back to its closed orientation, securely wrapping it about the user's wrist/forearm. As such, when the user pulls his or her arm out of the seal assembly 10, the iris seal 16 will automatically close sealing the body cavity from the external environment.

The second ratchet surface 68b allows the seal assembly 10 to be locked with the central access opening 46 in a larger open configuration allowing for more complete access to the body cavity. As those skilled in the art will certainly appreciate, it is at times desirable to provide a large access opening to the body cavity. As such, the present seal assembly 10 is provided with a second ratchet surface 68b providing for locking of the upper seal ring 32 and the lower seal ring 28 relative to each other when the iris seal 16 is more fully opened as shown in FIG. 6. As with the first ratchet surface 68a, the second ratchet surface 68b engages the ratchet arm 66 when the upper and lower seal rings 32, 28 are oriented in a particular orientation providing, in this case, a relatively large opening in the iris seal 16. A user rotates the upper seal ring 32 relative to the lower seal ring 28 to create an opening in the iris seal 16 beyond the small opening as shown in FIG. 5. Once the first ratchet surface 68a is passed (as indicated by the first series of audible clicks), the audible clicking sound produced as the ratchet arm 66 moves over the second ratchet surface 78b will provide the user with an indication a stopping position has been reached. At this point, the user may release the upper seal ring 32 without fear that the iris seal 16 will close, and proceed to utilize the large opening for access to the body cavity in a desired manner. When the user no longer requires this access, he or she may simply rotate the upper seal ring 32 relative to the lower seal ring 28 in a first direction slightly opening the iris seal 16 a little more, at which point the ratchet arm 66 will disengage from the second ratchet surface 68b and allow the upper seal ring 32 to rotate relative to the lower seal ring 28 under the bias of the spring 50 to move the iris seal 16 back to its closed orientation.

In accordance with an alternate embodiment and with reference to FIGS. 13 and 14, the upper seal ring 232 is seated within the track 230 of the lower seal ring 268 with the spring 250 biasing the upper seal ring 232 relative to the lower seal ring 268 for movement relative thereto opening and closing the central access opening 246. More particularly, and in accordance with a preferred embodiment, the track 230 includes an inner upstanding annular wall 230a and an outer upstanding annular wall 230b connected by an annular base member 230c. As discussed above, the ratchet mechanism includes a ratchet arm 266 coupled to the upper seal ring 232. The ratchet arm 266 is oriented to engage the first and second ratchet surfaces 268a, 268b coupled to lower seal ring 228. The first and second ratchet surfaces 268a, 268b are secured to an outer surface of the inner upstanding annular wall 230a such that the first and second ratchet surfaces 268a, 268b are positioned between the inner upstanding annular wall 230a and outer upstanding annular wall 230b. As those skilled in the art will certainly appreciate, it is contemplated the ratchet surfaces could also be secured to the inner surface of the outer upstanding annular wall and remain between the inner upstanding annular wall and the outer upstanding annular wall without departing from the spirit of the present invention.

The ratchet mechanism 248 is positioned between the upper seal ring 232 and the lower seal ring 268. The ratchet mechanism 248 includes a ratchet arm 266 secured to the upper seal ring 232. The ratchet arm 266 is oriented to engage first and second ratchet surfaces 268a, 268b composed of a plurality of ratchet teeth 270a, 270b on the lower seal ring 268. This interaction functions to hold the upper seal ring 232 relative to the lower seal ring 268 as it is moved to an open orientation. That is, the ratchet mechanism 248 controls the action of the spring 250 in urging the upper and lower seal rings 232, 268 back to their closed orientation. The ratchet arm 266 is shaped and dimensioned to engage the ratchet teeth 270a, 270b of the first and second ratchet surfaces 268a, 268b when rotated in a first direction (for example, and in accordance with a preferred embodiment, clockwise rotation when viewed from above). However, once the upper seal ring 232 is rotated such that the ratchet arm 266 moves beyond the rear end 272a, 272b of the first and second ratchet surfaces 268a, 268b, the ratchet arm 266 is free to move past the first and second ratchet surfaces 268a, 268b as the upper seal ring 232 is rotated in a second direction opposite the first direction under the biasing action of the spring 250 which urges the upper and lower seal rings 232, 268 to their closed orientation.

This is achieved by providing the ratchet arm 266 with a cut out section 274 and a tapered distal end 276 which is biased by a similar tapered surface 278a, 278b on the respective rear end 272a, 272b of the first and second ratchet surfaces 268a, 268b to ride under the first and second ratchet surfaces 268a, 268b as the upper seal ring 232 is rotated relative to the lower seal ring 268 in the second direction. However, when the upper seal ring 232 is rotated in a first direction, the distal end 276 of the ratchet arm 266 is biased to ride over the upper surface 290a, 290b of the first and second ratchet surfaces 268a, 268b such that it engages the various ratchet teeth 270a, 270b to control movement of the upper seal ring 232 relative to the lower seal ring 268.

In accordance with this embodiment as shown in FIGS. 13 and 14, the first and second ratchet surfaces 268a, 268b, and consequently, the ratchet teeth 270a, 270b are oriented to extend inwardly along the track 230 in which the upper seal ring 232 rides. By providing the first and second ratchet surfaces 268a, 268b in an inwardly facing manner, the footprint of the seal assembly may be reduced allowing for a more streamline and user friendly device.

In accordance with a preferred embodiment, first and second ratchet surfaces 268a, 268b are provided. The ratchet arm 266 engages the first ratchet surface 268a when the upper and lower seal rings 232, 268 are oriented to provide a relatively small opening in the iris seal 216 through which a medical practitioner may pass his or her hand to gain access to a body cavity (see, for example, FIG. 5). The configuration is especially suited to single hand interactions where a user may rotate the upper seal ring 232 relative to the lower seal ring 268 with the same hand which is to be passed through the present seal assembly 210. In particular, and as a result of the ratchet mechanism, a user may, for example, use his or her left hand to rotate the upper seal ring 232 relative to the lower seal ring 268 in a manner slightly opening the iris seal 216. When in this position, the audible click sound and slight resistance produced as the ratchet arm 266 moves over the internally oriented first ratchet surface 268a will provide the user with an indication a stopping position has been reached. The user may then release the upper seal ring 232 without fear that the iris seal 216 will snap back to its closed orientation under the control of the spring 250. Rather, the ratchet mechanism 248 holds the upper and lower seal rings 232, 268 relative to each other allowing the user to slip his or her hand through the opening in the iris seal 216. As the user pushes his or her hand through the iris seal 216, the outward force of the hand passing through the iris seal 216 causes a slight rotation of the upper seal ring 232 relative to the lower seal ring 268 in a manner disengaging the ratchet arm 266 from the first ratchet surface 268a. This allows the upper seal ring 232 to rotate relative to the lower seal ring 268 under the bias of the spring 250 to move the iris seal 216 back to its closed orientation, securely wrapping it about the users' wrist/forearm. As such, when the user pulls his or her arm from the seal assembly 210, the iris seal 216 will automatically close sealing the body cavity from the external environment. The second ratchet surface 268b allows the seal assembly 210 to be locked in a larger open configuration allowing for more complete access to the body cavity. As those skilled in the art will certainly appreciate, it is at times desirable to provide a large access opening to the body cavity. As such, the present seal assembly 210 is provided with a second ratchet surface 268b providing for locking of the upper seal ring 232 and the lower seal ring 268 relative to each other when the iris seal 216 is more fully opened as shown in FIG. 6 with reference to the prior embodiment. As with the first ratchet surface 268a, the second ratchet surface 268b engages the ratchet arm 266 when the upper and lower seal rings 232, 268 are oriented in a particular orientation providing, in this case, a relatively large opening in the iris seal 216. A user rotates the upper seal ring 232 relative to the lower seal ring 268 to create an opening in the iris seal 216 beyond the small opening as shown in FIG. 5. Once the first ratchet surface 268a is passed (as indicated by the first series of audible clicks), the audible clicking sound produced as the ratchet arm 266 moves over the second ratchet surface 268b will provide the user with an indication a stopping position has been reached. At this point, the user may release the upper seal ring 232 without fear that the iris seal 216 will close under the control of the spring 250, and proceed to utilize the large opening for access to the body cavity in a desired manner. When the user no longer requires this access, he or she may simply rotate the upper seal ring 232 relative to the lower seal ring 268 in a first direction slightly opening the iris seal 216, at which point the ratchet arm 266 will disengage from the second ratchet surface 268b and allow the upper seal ring 232 to rotate relative to the lower seal ring 268 under the bias of the spring 250 to move the iris seal 216 back to its closed orientation.

In accordance with an alternate embodiment and as shown with reference to FIGS. 15, 16, 17 and 18, the ratchet surfaces 368a, 368b are formed along the exterior surface 392 of the outer upstanding annular wall 330b of the lower seal ring 328 for engagement with a spring arm 366 internally extending along a downwardly extending flange of the upper seal ring 332. By providing the ratchet teeth 370a, 370b along the external surface 392, the apparatus is more easily molded and once again provides a relatively small footprint. Functioning of this embodiment is substantially identical to the embodiment described above with regard to FIGS. 13 and 14.

Further, and in accordance with this embodiment, the lower seal ring 328 is formed with a plurality of preformed recesses 396 in the outer upstanding annular wall 330b and around the circumference thereof. As such, assembly of the present seal assembly 310 is improved by allowing the user or manufacturer to selectively position one or a plurality of ratchet surfaces 368a, 368b at desired locations around the circumference of the lower seal ring 328. The ratchet surfaces 368a, 368b, are secured at desired locations within the recesses 396 by a snap lock attachment well known to those skilled in the art. This allows for adjustment in the opening rotation of the seal assembly 310 and adjustment of the lock positions provided by the seal assembly 310.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:
   a seal cap including a seal positioned within a housing, the housing including a lower seal ring having a track which supports an upper seal ring for relative rotational motion, wherein the seal is supported between the upper seal ring and the lower seal ring for rotation between an open orientation and a closed orientation;
   the track includes an inner upstanding annular wall and an outer upstanding annular wall connected by a base member, the outer upstanding annular wall including a plurality of preformed recesses formed therein; and
   a ratchet mechanism controlling motion of the upper seal ring relative to the lower seal ring, the ratchet mechanism including a ratchet arm oriented to engage a ratchet surface, the ratchet surface extends outwardly from a center of the seal assembly;
   wherein the ratchet arm is coupled to the upper seal ring and the ratchet surface is coupled to the lower seal ring, the ratchet surface being secured along an exterior surface of the outer upstanding annular wall at desired locations within the preformed recesses such that the ratchet surface extends outwardly from the center of the seal assembly.

2. The seal assembly according to claim 1, wherein the ratchet surface is secured within the preformed recess via a snap lock attachment.

3. The seal assembly according to claim 2, wherein the ratchet arm is shaped and dimensioned to engage the ratchet surface when the upper seal ring is rotated relative to the lower seal ring in a first direction and rides under the ratchet surface when the upper seal ring is rotated relative to the lower seal ring in a second direction.

4. The seal assembly according to claim 3, wherein the ratchet arm includes a tapered distal end shaped and dimensioned to ride under the ratchet surface as the upper seal ring is rotated relative to the lower seal ring in the second direction.

5. The seal assembly according to claim 4, further including first and second ratchet surfaces on the lower seal ring.

6. The seal assembly according to claim 1, further including first and second ratchet surfaces.

7. The seal assembly according to claim 1, further including a spring biasing the upper seal ring relative to the lower seal ring.

8. The seal assembly according to claim 1, further including a retractor extending from the seal cap.

9. The seal assembly according to claim 8, wherein the housing further includes an attachment ring detachably secured to the lower seal ring for permitting selective attachment of the retractor by positioning it between the attachment ring and the lower seal ring.

10. The seal assembly according to claim 9, wherein the lower seal ring includes at least one outwardly extending flange shaped and dimensioned for seating within at least one inwardly facing recess formed along the attachment ring.

11. The seal assembly according to claim 1, wherein an upper end of the seal is connected to the upper seal ring and a lower end of the seal is connected to the lower seal ring.

12. The seal assembly according to claim 1, further including an ergonomic cover member secured to the upper seal ring, wherein the ergonomic cover member includes a contoured outer surface providing for improved handling and twisting of the upper seal ring for opening and closing the seal.

13. The seal assembly according to claim 1, wherein the seal is an iris seal.

14. The seal assembly according to claim 13, wherein the iris seal is constructed in a folded configuration spanning the upper seal ring and the lower seal ring.

15. The seal assembly according to claim 13, wherein the iris seal is composed of a rubber like member.

16. The seal assembly according to claim 1, further including a contoured ring secured to the upper seal ring, the contoured ring including an inner circumference formed with a series of recesses shaped and dimensioned for receiving fingers of a user.

17. The seal assembly according to claim 1, wherein the outer upstanding annular wall includes a plurality of recesses shaped and dimensioned for selectively receiving the ratchet surface at desired locations along the lower seal ring.

18. The seal assembly according to claim 1, wherein the ratchet arm is shaped and dimensioned to engage the ratchet surface when the upper seal ring is rotated relative to the lower seal ring in a first direction and rides under the ratchet surface when the upper seal ring is rotated relative to the lower seal ring in a second direction.

19. The seal assembly according to claim 18, wherein the ratchet arm includes a tapered distal end shaped and dimensioned to ride under the ratchet surface as the upper seal ring is rotated relative to the lower seal ring in the second direction.

20. The seal assembly according to claim 19, further including first and second ratchet surfaces on the lower seal ring.

* * * * *